United States Patent [19]

Sievers et al.

[11] 3,970,561

[45] July 20, 1976

[54] SEPARATION OF COMPOUNDS DIFFERING IN ISOTOPIC COMPOSITION

[76] Inventors: Robert E. Sievers, 2628 N. Emerald Drive, Fairborn, Ohio 45324; Joseph J. Brooks, 1631 Beaver Ridge Drive, Kettering, Ohio 45429

[22] Filed: Mar. 11, 1975

[21] Appl. No.: 557,568

Related U.S. Application Data

[62] Division of Ser. No. 476,179, June 4, 1974, Pat. No. 3,891,413.

[52] U.S. Cl. ............................ 210/198 C; 55/386; 210/502; 252/462
[51] Int. Cl.² ..................................... B01V 15/08
[58] Field of Search ................... 55/67, 386, 524; 210/24 C, 198 C, 502; 252/259.5, 462; 427/217, 230, 237

[56] References Cited

UNITED STATES PATENTS

3,488,921  1/1970  Inchauspe ........................... 55/67 X

OTHER PUBLICATIONS

Gas Phase Chromatography 3 by Kaiser, Butterworth & Co. 1963, pp. 22–43.

*Primary Examiner*—John Adee
*Attorney, Agent, or Firm*—Joseph E. Rusz; Cedric H. Kuhn

[57] ABSTRACT

Compounds differing in isotopic composition are separated by introducing a mixture of the compounds into a chromatographic column containing a lanthanide chelate as a stationary phase and eluting from the column a fraction which is at least enriched with one of the compounds of the mixture.

17 Claims, No Drawings

SEPARATION OF COMPOUNDS DIFFERING IN ISOTOPIC COMPOSITION

RIGHTS OF THE GOVERNMENT

There is reserved to the Government of the United States a nonexclusive, irrevocable, royalty-free license in the invention described herein with power to grant licenses for all governmental purposes.

This application is a division of copending application Ser. No. 476,179, filed on June 4, 1974, now U.S. Pat. No. 3,891,413.

FIELD OF THE INVENTION

This invention relates to a process for separating from one another compounds containing an electron donor group and differing in isotopic composition. In one aspect, it relates to a process for separating from one another oxygen-containing compounds having a donor group and differing only in degree and/or position of deuteration.

BACKGROUND OF THE INVENTION

In Canadian Journal of Chemistry, 45, 1963–1969; (1967), J. G. Atkinson et al disclose the use of long, silver nitrate-ethylene glycol gas chromatographic columns to separate deuterated olefins differing by only one deuterium atom. Also, V. Schurig et al., in Chromatographia, 6, No. 5, 223–225, (1973), disclose the use of dicarbonylrhodium-3-trifluoroacetyl-d-camphorate as the stationary phase in gas-liquid chromatography in which olefins, including ethylene and deuterated ethylene were separated. While these prior art methods can be used in the separation of unsaturated compounds, such as olefins, they are not suitable for use in the separation of organic compounds containing functional groups, such as hydroxyls in alcohols, and differing in isotopic composition.

It is an object of this invention, therefore, to provide a process for separating organic compounds containing an electron donor group that differ in isotopic composition.

Another object of the invention is to provide a process for separating a deuterated organic compound having an electron donor group from an isotopic mixture of organic compounds having an electron donor group.

A further object of the invention is to provide a process for the analysis of the products of deuteration reactions.

Still another object of the invention is to provide a process for detecting small quantities of non-deuterated, partially deuterated or totally deuterated organic compounds in the presence of other compounds differing only in the degree of deuteration. A still further object of the invention is to provide a process for the separation of isotopes contained in any compound or moiety which can interact to differing degrees with a lanthanide chelate, thereby affording the physicochemical basis for a separation or enrichment.

Other objects and advantages of the invention will become apparent to those skilled in the art upon consideration of the accompanying disclosure.

SUMMARY OF THE INVENTION

The present invention resides in a process for separating compounds differing in isotopic composition. The process comprises the steps of introducing a mixture of the compounds into a chromatographic column containing a lanthanide chelate as a stationary phase, and eluting from the column a fraction at a particular point in time that is at least enriched with respect to one of the compounds of the mixture. The process is particularly applicable to the separation of a deuterated isomer from an isotopic mixture of organic compounds containing an electron donor group. The invention is based upon the discovery that two or more of such compounds differing only in isotopic composition, i.e., deuterium atom or atoms substituted for hydrogen atom or atoms, exhibit significant differences in the degree of interaction with the lanthanide chelates. The different degrees of interaction result in different retention times in the chromatographic column, thereby making it possible to separate the components of an isotopic mixture or to recover a product enriched with respect to one of the components.

The lanthanide chelates that can be used in the practice of the present invention can be represented by the following structural formula:

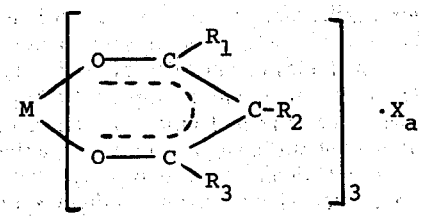

wherein M is a rare earth element of the lanthanide series; $R_1$, $R_2$, and $R_3$ are individually selected from the group consisting of hydrogen, deuterium, alkyl and fluoroalkyl, or $R_1$ and $R_2$ together are d-camphor and $R_3$ is fluoroalkyl; X is water or an organic compound containing a donor group; and $a$ is a numeral from zero to 4, inclusive. The alkyl and fluoroalkyl groups contain 1 to 10, inclusive, preferably from 1 to 4, inclusive, carbon atoms.

As indicated in the above paragraph, the letter "X" represents water or an organic compound containing a donor group that combines in molecular form with the lanthanide chelate. Examples of organic compounds include methanol, acetone, dimethylformamide, dimethoxypropane, and the like. In the practice of the present process, it is usually preferred to use a lanthanide chelate which is not complexed with water or an organic compound, i.e., the letter "$a$" in the foregoing formula equals zero. The rare earth chelate may exist in monomeric, dimeric, trimeric or polymeric form so long as it is still capable of functioning as a Lewis acid.

The letter "M" in the foregoing formula represents the trivalent rare earth ions. The ions and their symbols in the order of their atomic numbers are lanthanum (La), cerium (Ce), praseodymium (Pr), neodymium (Nd), samarium (Sm), europium (Eu), gadolinium (Gd), terbium (Tb), dysposium (Dy), holmium (Ho), erbium (Er), thulium (Tm), ytterbium (Yb), lutetium (Lu), and yttrium (Y).

Examples of lanthanide chelates corresponding to the foregoing formula include tris(1,1,1,2,2,3,3-heptafluoro-7,7-dimethyloctane-4,6-dionato)europium(III) [Eu(fod)$_3$]; tris(2,4-pentanedionato)yttrium-(III)trihydrate; tris(benzoylacetonato)yttrium(III)hydrate; tris(2,4-pentanedionato)lanthanum(III)dihydrate; tris(1,1,1,2,2,3,3-heptafluoro-7,7-dimethyloctane-4,6- dionato)praseodymium(III) [Pr(fod)$_3$]; tris(1,1,1,2,2,3,3,7,7,7-decafluoro-4,6-heptanedionato)europium(III)dihydrate; tris(1,1,1,2,2,3,3,7,7,7-decafluoro-4,6-heptanedionato-ytterbium(III); tris(1,1,1,2,2,3,3,3-heptafluoro-7,7-dimethyloctane-4,6-dionato)ytterbium(III); dimethylformamide adduct of tris(1,1,1,-5,5,5-hexafluoro-2,4-pentanedionato)europium(III); perdeuterated tris(1,1,1,2,2,3,3-heptafluoro-7,7-dimethyloctane-4,6-dionato)praseodymium(III); tris(trifluoroacetyl-d-camphorato)europium(III); and the like.

The lanthanide chelates represented by the above formula and methods for their synthesis are described in the literature. In this regard attention is directed to Inorganic Chemistry, 6, 1105 (1967), Inorganic Chemistry, 10, 498 (1971) and U.S. Pat. No. 3,700,410, which are incorporated herein by reference.

In general, the process of this invention is applicable to the separation of isotopic mixtures of organic compounds having electron donor groups. Classes of such compounds include ether, esters, ketones, alcohols, amines, acids, amino acid derivatives, oximes, sulfides, sulfoxides, nitriles and amides as well as various natural products. Specific examples of compounds of the aforementioned classes include the following: ethyl ether, di-n-butyl ether, methyl n-propyl ether, methyl tert-propyl ether, n-propyl ether, tert-butyl ether, 1-chloroethyl ethyl ether, vinyl ether, vinyl methyl ether, vinyl ethyl ether, allyl ether, ethynyl ethyl ether, benzyl methyl ether, benzyl ethyl ether; 2-ethylhexyl acetate, hexyl acetate, isoamyl acetate, ethyl propionate, ethyl acetate, butyl acetate, isopropyl acetate, benzyl acetate, benzyl propionate, methyl benzoate, methyl formate, triethyl orthoformate, ethyl acetoacetate; methyl n-propyl ketone, acetone, methyl ethyl ketone, diisobutyl ketone, methyl vinyl ketone, acetopropanol, chloroacetone, chloropentanone, cyclohexanone, isophorone, acetophenone, acrylophenone; ethanol, isopropanol, secondary butanol, methylethyl carbinol, pentanol, tertiary butyl carbinol, n-hexyl alcohol, n-octyl alcohol, n-decyl alcohol, cyclohexanol, allyl alcohol, ethylphenyl alcohol, benzyl alcohol, menthol, glycerol; methylamine, isopropylamine, n-butylamine, allylamine, dimethylamine, diisopropylamine, di-n-amylamine, methylethylamine, trimethylamine, tri-n-butylamine, cyclohexylamine, aniline, diphenylamine, 2-aminopyridine; formic, acetic, butyric, and acrylic acids; dimethyl sulfide, methylene sulfide, diethyl sulfide, divinyl sulfide, diallyl sulfide, dichloro ethyl sulfide, acetyl disulfide; phenyl sulfoxide, dimethyl sulfoxide, diphenyl sulfoxide; acetonitrile, butyronitrile, isobutyronitrile, acrylonitrile; formamide, dimethylacetamide, dimethylformamide, trifluoroacetyl amides derived from amino acids (e.g., trifluoroacetylalamine); and the like. Examples of natural products include camphor, lanosterol, testosterone, DDE (metabilite of DDT), andosterone and cholesterol. Examples of pollutants and isotopic pollutant tracers that can be separated by the practice of this invention include peroxyacylnitrate, acetaldehyde, benzaldehyde, formaldehyde, isoamyl alcohol, ethyl acetate, n-propanol, isopropanol, dieldrin and butyric acid.

The various procedures followed in the separation of the components of a mixture by column chromatography are well known and are described in the literature, e.g., in Van Nostrand's Scientific Encyclopedia, 4th Edition, pages 342–346. Although it will be recognized that there are other differences, the principal difference in the various procedures resides in the stationary and moving phases employed. In general, the process of this invention can be carried out by gas-liquid, liquid-solid or liquid-liquid chromatography in each of which a lanthanide chelate, as defined herein, functions as the stationary phase.

In a preferred embodiment, gas-liquid chromatography is utilized in the separation of the components of isotopic mixtures by the present process. Prior to actual conduct of the process, the column is prepared. Firstly, the lanthanide chelate to be used is added to a solvent therefor that is preferably a high molecular weight hydrocarbon, such as squalane, squalene, or a mixture of high molecular weight aliphatic hydrocarbons sold by Associated Electrical Industries, Ltd. under the trade marks Apiezon L and Apiezon N. Other solvents that can be employed include polysiloxanes, such as those sold by Dow Corning under the code names DC-550 and DC-710 and by General Electric under the designation SE-30, and perhalogenated polymers, such as Kel-F grease and Kel-F oil sold by Applied Science Laboratories, Inc. The solution is then diluted by adding thereto a low molecular weight solvent for the lanthanide chelate and liquid stationary phase, such as chloroform, carbon tetrachloride, methylene chloride or benzene.

The diluted solution of the lanthanide chelate is mixed with a solid support material. Examples of suitable support materials include acid washed, silanized diatomaceous earths, e.g., those sold by Johns Manville Corp. under the trade marks Chromosorb P, Chromosorb W and Gas Chrom Z sold by Applied Science Laboratories, Inc., glass beads, and porous polymers, such as open pore polyurethanes and polystyrene-divinylbenzene copolymers. After thoroughly mixing the materials, the diluent is removed, e.g., by evaporation, leaving the support material coated with the solution of lanthanide chelate. The amount of solution coated on the support material generally ranges from about 0.5 to 20 weight percent, based on the weight of the support material. The concentration of lanthanide chelate can range from that sufficient to provide an 0.05 molal solution to an amount sufficient to provide a saturated solution. The amount of lanthanide chelate required to provide a saturated solution will vary with the particular chelate and solvent used, but it is well within the skill of the art to prepare a solution containing a concentration of chelate in the aforementioned range.

The support material coated with the solution of a lanthanide chelate is next packed into a chromatographic column. Thereafter, the packed column, which can be in the form of stainless steel, copper, glass, nylon or Teflon tubing, is then connected to a gas chromatograph. The chromatograph is conventionally provided with an injection port, a heating means, a thermostat, a flame ionization, thermal conductivity or other suitable detector, and a recording means.

Initially, the column is conditioned by passing a carrier gas through the column for a period of time sufficient to remove any trace impurities from the column. The period of time required to condition a column usually ranges from about 4 to 72 hours. An inert gas, such as nitrogen, helium or argon, is used as the carrier gas. During the conditioning process, the column is heated to about 5° to 15°C above the temperature at which it is intended to operate the column during the separation process.

After the column is conditioned, the isotopic mixture to be separated into its deuterated, partially deuterated and non-deuterated components is introduced into the column through the injection port. The injection port is preheated to a temperature high enough to vaporize the mixture, and this temperature will necessarily depend upon the particular mixture being used. During conduct of the separation process, the carrier gas is injected into and flowed through the column at a constant rate, thereby sweeping the vaporized isotopic mixture into and through the column. The temperature of the column is such as to maintain a vapor phase therein and to cause reasonably rapid elution. While the isotopic mixture is in the column, an equilibrium exists between the stationary liquid phase and the vapor phase so that molecules are continually being transferred from the vapor phase to the liquid phase and vice versa. While the molecules are in the vapor or moving phase, they are swept further through the column. When the molecules are in the stationary liquid phase, they interact with the lanthanide chelate molecules to form complexes reversibly. It has been discovered that components of the mixture differing only in isotopic composition exhibit significant differences in the degree of interaction with the lanthanide chelate. This results in the strongly interacting compounds being retained in the liquid phase for longer periods of time, causing these compounds to have a longer retention time in the column. Thus, it has been found that the deuterated isotope has a longer retention time than the non-deuterated isotope of organic compounds having an electron donor group.

The actual retention times of the components is determined by means of the flame ionization or other suitable detector which is operatively connected to a recording system. By means of the recording system, a graphical indication of the retention times is obtained. Thereafter, the detector may be inactivated and the different fractions of the effluent from the column are collected on the basis of the known retention times which are characteristic of the different components of the isotopic mixture. These fractions can be collected by passing the effluent gas stream through a series of condensers appropriately cooled, e.g., by ice, dry ice or liquid nitrogen, that are rotated to switch connections sequentially at the specific times when the desired isotopic species is being eluted. Control systems are commercially available for separately recovering the different components of a mixture that are sequentially eluted from a chromatographic column.

It is within the scope of the present invention to utilize a so-called SCOT column as well as conventional packed column. The SCOTT column is a narrow bore column in which the support material is coated on the wall of the column. The stationary phase is formed by filling the column with the diluted solution of a lanthanide chelate. Upon removing excess solution and evaporating the remaining diluent by passing a stream of carrier gas through the column, the support material is impregnated with the remaining non-volatile material. The process of this invention is then carried out in essentially the same manner as described above.

A column in the form of a capillary tube can also be employed in which a support material is not required. With a capillary tube the solution of the lanthanide chelate is coated on the wall of the tube. This can be conveniently accomplished by filling the tube with a dilute solution of a lanthanide chelate and a relatively non-volatile liquid stationary phase dissolved in a more volatile solvent such as chloroform. After removing the diluent, e.g., by evaporation, the tube remains coated with the solution which functions as the stationary phase as described above.

In liquid-liquid chromatography, the isotopic mixture is introduced into a column in a liquid which is not a good solvent for the particular lanthanide chelate (e.g., tris(2,4-pentanedionato)lanthanium(III) dihydrate), such as cyclohexane, isooctane and the like. As described above with regard to gas chromatography, the stationary phase is a solution of the lanthanide chelate. However, the moving phase is a liquid rather than a gas although the column operates in essentially the same manner. The isotopic mixture of interest can eventually be separated from the liquid used as an eluting solvent by fractional distillation.

A better understanding of the invention can be obtained by referring to the following illustrative examples which are not intended, however, to be unduly limitative of the invention.

EXAMPLE I

Experiments were conducted using an F&M Model 810 gas chromatograph equipped with a flame ionization detector for the purpose of determining the retention times of 2-butanol, $CH_3CH(OH)CH_2CH_3$, and $d_1$, 2-butanol, $CH_3CD(OH)CH_2CH_3$. A 12-inch column of heavy walled Teflon tubing having an inside diameter of ⅛ inch was used. The column was packed with 60/80 mesh Gas Chrom Z coated 15 percent by weight with 0.13 molal $Eu(FOD)_3 \cdot H_2O$ in squalane. The 2-butanol and $d_1$, 2-butanol were injected into the column as vapors which were drawn from above the liquids using a 10 $\mu$l syringe. Data were collected at a column temperature of 87°C and a helium carrier gas flow rate of 60 ml/min. Under these conditions 2-butanol and $d_1$, 2-butanol had average retention times of 197.6 and 204.7 seconds, respectively. This represents a 7.1 seconds or 3.5 percent difference in the retention times for the two compounds, indicating that the $d_1$, 2-butanol interacts more strongly with the $Eu(FOD)_3$ than does the 2-butanol.

A control run was conducted in which essentially the same procedure as described above was followed except that the support material was coated only with squalane. Under these conditions, i.e., in the absence of $Eu(FOD)_3$, the 2-butanol and $d_1$, 2-butanol had the same retention times.

EXAMPLE II

Runs were carried out following the procedure described in Example I in which 2-octanol and $d_1$, 2-octanol, and 2-propanol and $d_8$, 2-propanol were used instead of 2 butanol and $d_1$, 2-butanol. Results similar to those of Example I were obtained with the deuterated species always being retained longer.

As seen from the foregoing data, the present invention provides a process for separating non-deuterated from deuterated species of isotopic mixtures of organic compounds containing electron donors. The use of partially or totally deuterated organic compounds is important in labelling compounds for identification purposes. The deuterated compounds are also useful as solvents in analyzing compounds by nuclear magnetic resonance since they do not interfere with the NMR signal of the compound being investigated. The prior art methods for separating deuterated organic compounds generally involve expensive and time-consuming distillation procedures or special reaction procedures. The process of the present invention provides an inexpensive and relatively rapid process for the separation and purification of such compounds.

As will be evident to those skilled in the art, variations and modifications of the invention can be made by those skilled in the art in view of the foregoing disclosure without departing from the spirit and scope of the invention.

We claim:

1. A composition consisting essentially of a particulate support material and a solution of a lanthanide chelate coated thereon, the lanthanide chelate having the following structural formula:

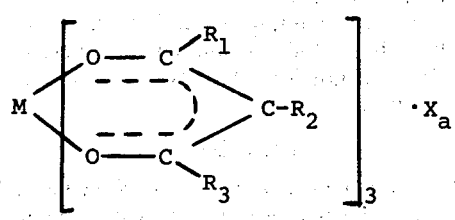

wherein M is a rare earth element of the lanthanide series; $R_1$, $R_2$ and $R_3$ are individually selected from the group consisting of hydrogen, deuterium, alkyl and fluoroalkyl; $R_1$ and $R_2$ together are d-camphor and $R_3$ is fluoroalkyl; X is water or an organic compound containing a donor group; and $a$ is a numeral from zero to 4, inclusive.

2. The composition according to claim 1 in which the lanthanide chelate is tris(1,1,1,2,2,3,3,3-heptafluoro-7,7-dimethyloctane-4,6-dionato)europium(III).

3. The composition according to claim 1 in which the lanthanide chelate is tris(1,1,1,2,2,3,3,3-heptafluoro-7,7-dimethyloctane-4,6-dionato)praseodymium(III).

4. The composition according to claim 1 in which the lanthanide chelate is tris(1,1,1,2,2,3,3,7,7,7-decafluoro-4,6-heptanedionato)-europium(III)dihydrate.

5. The composition according to claim 1 in which the lanthanide chelate is tris(1,1,1,2,2,3,3,7,7,7-decafluoro-4,6-heptanedionato)-ytterbium(III).

6. The composition according to claim 1 in which the lanthanide chelate is tris(2,4-pentanedionato)lanthanum(III)dihydrate.

7. The composition according to claim 1 in which the support material is selected from the group consisting of acid washed, silanized diatomaceous earths, glass beads, and porous polymers.

8. The composition according to claim 7 in which the lanthanide chelate is in solution in a high molecular weight hydrocarbon.

9. The composition according to claim 1 in which the amount of solution coated on the support material ranges from about 0.5 to 20 weight percent, based on the weight of the support material, and the concentration of the lanthanide chelate in the solution ranges from an amount sufficient to provide an 0.05 molal solution to an amount sufficient to provide a saturated solution.

10. In a chromatographic column, a stationary phase comprising a lanthanide chelate having the following structural formula:

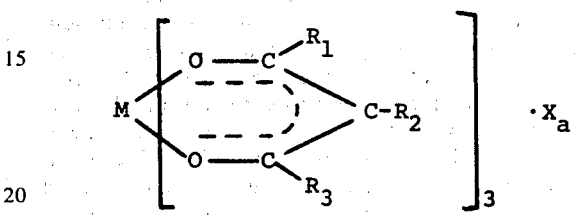

wherein M is a rare earth element of the lanthanide series; $R_1$, $R_2$ and $R_3$ are individually selected from the group consisting of hydrogen, deuterium, alkyl and fluoroalkyl; or $R_1$ and $R_2$ together and d-camphor and $R_3$ is fluoroalkyl; X is water or an organic compound containing a donor group; and $a$ is a numeral from zero to 4, inclusive.

11. The stationary phase according to claim 10 in which the lanthanide chelate is tris(1,1,1,2,2,3,3,3-heptafluoro-7,7-dimethyloctane-4,6-dionato)europium(III).

12. The stationary phase according to claim 10 in which the lanthanide chelate is tris(1,1,1,2,2,3,3,3-heptafluoro-7,7-dimethyloctane-4,6-dionato)-praseodymium(III).

13. The stationary phase according to claim 10 in which the lanthanide chelate is tris(1,1,1,2,2,3,3,7,7,7-decafluoro-4,6-heptanedionato)europium(III)dihydrate.

14. The stationary phase according to claim 10 in which the lanthanide chelate is tris(1,1,1,2,2,3,3,7,7,7-decafluoro-4,6-heptanedionato)ytterbium(III).

15. The stationary phase according to claim 10 in which the lanthanide chelate is tris(2,4-pentanedionato)lanthanum(III)dihydrate.

16. The stationary phase of claim 10 which consists essentially of a solution of the lanthanide chelate coated on a particulate support material which is packed in the column.

17. The stationary phase of claim 10 which consists essentially of a solution of the lanthanide chelate coated on the inside wall of the column.

* * * * *